United States Patent
Gallegos

(10) Patent No.: US 6,423,021 B1
(45) Date of Patent: Jul. 23, 2002

(54) ANKLE BRACE

(75) Inventor: Alvaro Gallegos, Albuquerque, NM (US)

(73) Assignee: Z-Coil, Albuquerque, NM (US)

( * ) Notice: Subject to any disclaimer, the term of this patent is extended or adjusted under 35 U.S.C. 154(b) by 0 days.

(21) Appl. No.: 09/874,963

(22) Filed: Jun. 7, 2001

(51) Int. Cl.$^7$ ................................................ A61F 5/00
(52) U.S. Cl. .......................................... 602/23; 602/27
(58) Field of Search .................................. 128/846, 864, 128/882; 602/5, 23, 27

(56) References Cited

U.S. PATENT DOCUMENTS

| | | | | |
|---|---|---|---|---|
| 6,214 A | * | 3/1849 | Yerger | 602/27 |
| 589,253 A | * | 8/1897 | Engberg | 602/27 |
| 839,223 A | | 12/1906 | Stevens | |
| 1,332,047 A | * | 2/1920 | Lasher | 602/27 |
| 1,336,001 A | * | 4/1920 | Tranmer | 602/27 |
| 1,354,427 A | | 9/1920 | Welter | |
| 1,598,504 A | | 8/1926 | Pierce et al. | |
| 4,938,777 A | | 7/1990 | Mason et al. | |
| 5,329,705 A | | 7/1994 | Grim et al. | |
| 5,593,383 A | | 1/1997 | DeToro | |
| 5,672,156 A | | 9/1997 | Jimenez Ramos | |
| 5,792,087 A | | 8/1998 | Pringle | |

\* cited by examiner

*Primary Examiner*—Michael A. Brown
(74) *Attorney, Agent, or Firm*—Oliff & Berridge, PLC

(57) ABSTRACT

An ankle brace and shoe therefor allows substantial forward and rearward movement of an ankle while substantially limiting side-to-side motion of the ankle. The ankle brace includes a semi-rigid orthotic plate shaped to receive a wearer's ankle thereon and having a rear support portion. At least one axial slip support bracket having an opening therethrough is fixedly provided on the rear support portion. A longitudinally extending blade element is slidably attachable to the at least one axial slip support bracket at a proximal end thereof and substantially fixed relative to a leg of the wearer by at least one support member at a distal end thereof. The blade element has an axial length, a thickness T extending in a fore/aft direction of the orthotic plate corresponding to a fore/aft direction of a wearer's foot, and a width W. The ratio of T to W is selected so that the distal end is free to flex about the proximal end in the fore/aft direction and the blade element is substantially constrained from flexure in the width direction. A nominal clearance between the blade element and the opening of the at least one axial slip support bracket is chosen so that slide movement of the blade element through the opening along the longitudinal axis is allowed but lateral movement in the width direction is substantially constrained. The combination of clearance and ratio of T/W controls side-side movement allowed by the ankle brace.

23 Claims, 5 Drawing Sheets

ANKLE BRACE

BACKGROUND OF THE INVENTION

1. Field of Invention

The invention relates to an ankle brace and footwear containing such a brace that restricts side motion of an ankle while allowing less restricted control of forward and rearward ankle motion.

2. Description of Related Art

The ankle joint is capable of two types of pivotal movement of the ankle bone (talus) about the leg bone. This first is dorsiflexion and plantarflexion movement (forward/rearward). The second is inversion or eversion (side-to-side). Various combinations of these permit full movement of the ankle. However, excessive movements, particularly in inversion, can cause ankle sprain.

Ankle braces are known that assist or restrict certain movements of an ankle. Such devices have included standalone orthotic devices and orthotic devices incorporated into footwear. However, many such devices are overly restrictive and useful for rehabilitation purposes only, as normal or athletic movements cannot be attained. Others while allowing more mobility are overly bulky, uncomfortable, and difficult to mount on or wear with shoes.

SUMMARY OF THE INVENTION

There is a need for a simple, yet effective ankle brace that can restrict side-to-side motion of an ankle while allowing a large amount of forward and rearward movement.

There also is a need for an ankle brace having a blade element that freely flexes about a fixed axis to follow forward and rearward movement of an ankle while restricting rotation transverse to this axis.

The present invention overcomes various problems of the art and provides an ankle brace comprising: a semi-rigid orthotic plate shaped to receive a wearer's ankle or foot thereon, the orthotic plate having an upwardly extending rear support portion; at least one axial slip support bracket having an opening therethrough fixedly provided on the rear support portion; and a longitudinally extending blade element slidably attachable to the at least one axial slip support bracket at a proximal end thereof and substantially fixed relative to a leg of the wearer by at least one fixed support member at a distal end thereof. The blade element has an axial length, a thickness T extending in a fore/aft direction of the orthotic plate corresponding to a fore/aft direction of a wearer's foot, and a width W. The ratio of T to W is selected so that the distal end is free to flex about the proximal end in the fore/aft direction and the blade element is substantially constrained from flexure in the width direction. A clearance between the blade element and the opening of the at least one axial slip support bracket is chosen so that slide movement of the blade element through the opening along the longitudinal axis is allowed but lateral movement in the width direction is constrained.

The present invention also provides a shoe having an integrated ankle brace, comprising: a semi-rigid orthotic plate shaped to receive a wearer's ankle or foot thereon, the orthotic plate having an upwardly extending rear support portion; a shoe upper affixed to the orthotic plate; a sole portion located beneath the shoe upper; a heel portion located beneath the orthotic plate; at least one axial slip support bracket having an opening therethrough fixedly provided on the rear support portion; and a longitudinally extending blade element slidably attachable to the at least one axial slip support bracket at a proximal end thereof and substantially fixed relative to a leg of the wearer by at least one fixed support member at a distal end thereof. The blade element has an axial length, a thickness T extending in a fore/aft direction of the orthotic plate corresponding to a fore/aft direction of a wearer's foot, and a width W. The ratio of T to W is selected so that the distal end is free to flex about the proximal end in the fore/aft direction and the blade element is substantially constrained from flexure in the width direction. A clearance between the blade element and the opening of the at least one axial slip support bracket is chosen so that slide movement of the blade element through the opening along the longitudinal axis is allowed but lateral movement in the width direction is constrained.

BRIEF DESCRIPTION OF THE DRAWINGS

The foregoing and further objects, features and advantages of the invention will become apparent from the following description of preferred embodiments with reference to the accompanying drawings, wherein like numerals are used to represent like elements and wherein.

DETAILED DESCRIPTION OF PREFERRED EMBODIMENTS

Figure 1:
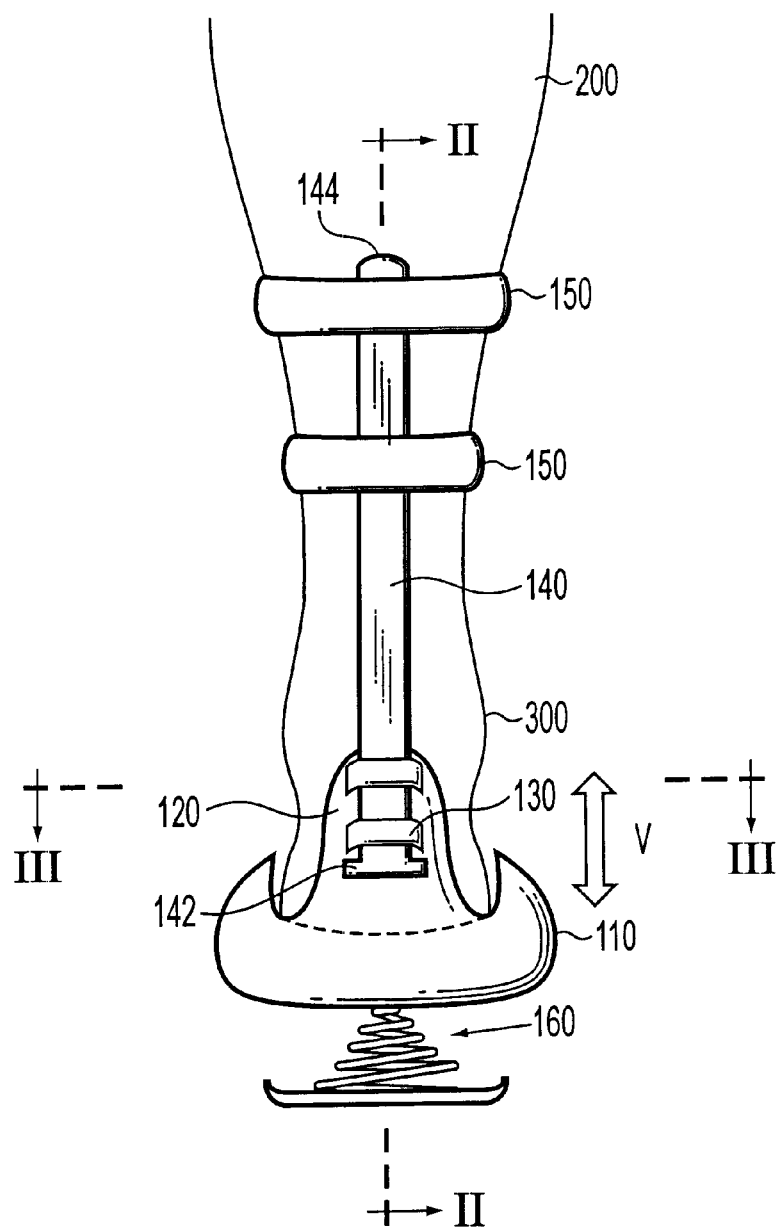
FIG. 1 is a rear view of an ankle brace according to the invention.
Figure 2:
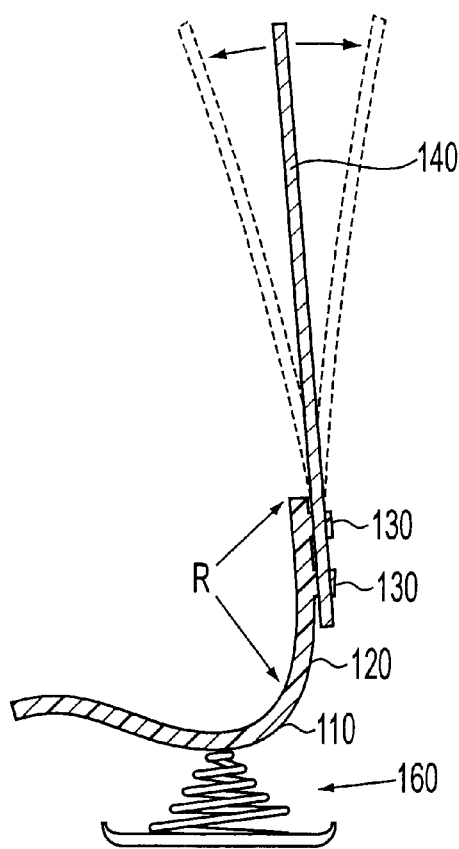
FIG. 2 is a partial cross-sectional view of the ankle brace of FIG. 1 taken along line II—II.
Figure 3:
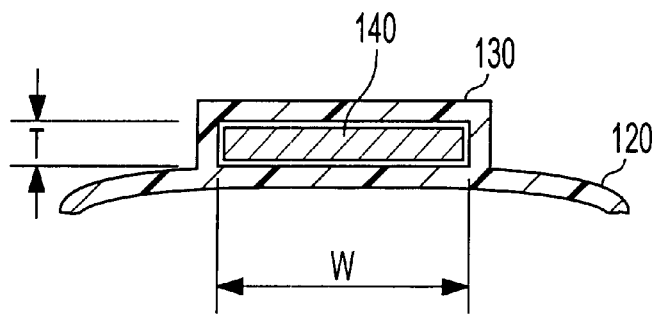
FIG. 3 is a cross-sectional view of the ankle brace of FIG. 1 taken along line III—III.

An exemplary embodiment of the invention will be described with reference to FIGS. 1–4. FIGS. 1–2 show a rear view and a cross-sectional view, respectively, of an illustrative ankle brace 100 according to the invention. Brace 100 include a rigid or semi-rigid orthotic plate 110 designed to receive at least an ankle 300 of a wearer thereon, an upwardly extending rear support portion 120 including at least one axial slip support bracket 130 defining an opening sized to receive a leg blade element 140 therethrough, at least one fixed support member 150 provided to at least removably affix a distal end 144 of blade element 140 relative to a leg 200 of the wearer, and an optional spring heel element 160 located on an underside of orthotic plate 110.

Blade element 140 has a predetermined width W and thickness T, at least in the vicinity of proximal end 142, sized to slip fit within the opening of slip support bracket 130. The width W and thickness T are selected relative to the size of the opening in slip support bracket 130 so that blade element 140 near proximal end 142 is only capable of slip movement along the longitudinal axis of blade element 140 and is substantially constrained from lateral side to side translational or rotational movement. To achieve this, there must be only a nominal clearance between edges of blade element 140 and the opening. To increase the freedom of axial movement while minimizing the need for increased clearance, either or both of support bracket 130 and blade element 140 may be coated with a low coefficient of friction material such as Teflon (polytetrafluoroethylene).

Width W and thickness T are also selected so that distal end 144 is fairly free to flex about proximal end 142 in the thickness direction (FIG. 2), which corresponds to forward/rearward movement of the ankle, while being constrained from flexure in the width direction. That is, by orienting the thickness direction to coincide with the fore/aft direction of the wearer's foot and the orthotic plate, blade element 140 is able to flex to allow a full range of forward/rearward motion of a wearer's ankle 300 and accommodate rotational movement of leg 200 relative to ankle 300 as shown in FIG. 2. The W and T selected are based on the characteristic properties of the blade material chosen and based on a desired amount of flexure (i.e., how much inversion and eversion are desired). If full freedom of ankle movement in the forward/rearward direction is desired, the flexure will of course be greater than if more restrictive movement is contemplated for a desired ankle brace design. However, it is preferable that the side-to-side motion is substantially restrained so as to produce little or no side-to-side movement.

Blade element 140 may be made of any suitable unitary or composite material capable of achieving such benefits and properties. Examples of such are semi-rigid metals, plastics, or composites including but not limited to aluminum, spring steel, metal alloys, fiber glass, nylon, PVC and the like. In an exemplary embodiment, blade element 140 has a width of about 33 mm and a thickness of about 3 mm. The opening in slip support brackets 130 in this exemplary embodiment has a nominal clearance that allows axial slip while preventing substantially all side-to-side motion of blade element 140.

Due to the designed rigidity of blade element 140 and the close tolerance fit of blade element 140 within slip support bracket 130, side-to-side motion of ankle 300 can be constrained to a controlled degree, which in many cases may be no side-to-side movement or only negligible side-to-side movement. The tolerance of the fit will, of course, be dictated by the desired restriction of side-to-side movement.

Orthotic plate 110 can be formed from any suitable rigid or semi-rigid material, such as plastic, hardened rubber, metal, reinforced polymers, composite materials, etc. Orthotic plate 110 is shaped to surround at least a lower portion of ankle 300 and extend toward a toe region of a wearer's foot. Rear support portion 120 of orthotic plate 110 extends upward behind ankle 300 and is preferably arcuate with a defined radius of curvature that generally coincides with a centroid or pivot point of a wearer's ankle 300. For the average adult, a preferred radius R is about 55 mm. However, radius R is not limited to this and may be less or greater than this depending on the size of ankle 300. For example, a child's orthotic plate would have a proportionally smaller radius.

The at least one axial slip support bracket preferably includes two spaced brackets as shown. These may be integrally formed into rear support portion 120 or may be separately formed and fixedly attached to rear support portion by suitable fasteners.

In this embodiment, fixed support member 150 may be one or more leg strap members that include Velcro, snaps, buckles, clasps or other releasable closing mechanisms to secure the strap around leg 200. Support member 150 may be fixed to blade element 140 or may be loosely fittable around blade element 140 and leg 200. Support member 150 is designed to constrain distal end 144 from axial movement along the leg while retaining fixture relative to the leg.

During use of brace 100, distal end 144 of blade element 140 remains at a substantially constant position relative to leg 200 due to fixture of support member 150 about leg 200. No appreciable axial movement of distal end 144 relative to the leg occurs during use. To accommodate full up/down movement of ankle 300 during walking or running, it becomes necessary to accommodate the change in lengths between distal end 144 and slip support brackets 130 during such movements, as well as accommodating fore/aft movement of leg 200. This is achieved by slip support brackets 130, which allow blade element 140 to slide with one degree of freedom (along the longitudinal axis of blade element 140) and the flexure of blade element 140. To prevent over-travel and removal of blade element 140 from slip support brackets 130, proximal end 142 may be of an increased width W or thickness T to prevent removal as shown in FIG. 1.

As full movement of ankle 300 can result in a change in length of between 1–1.5 inches (25–38 mm), there should be at least this amount of free length extending between the bottom of slip support brackets 130 and proximal end 142 when the blade element is in a most compressed state. However, if controlled restricted movement of ankle 300 is desired, this free length can be accordingly shortened. Additional control of movement can be attained by placing a wider portion similar to proximal end 142 at a position above slip support braces 130 to limit movement in either direction.

Figure 4:
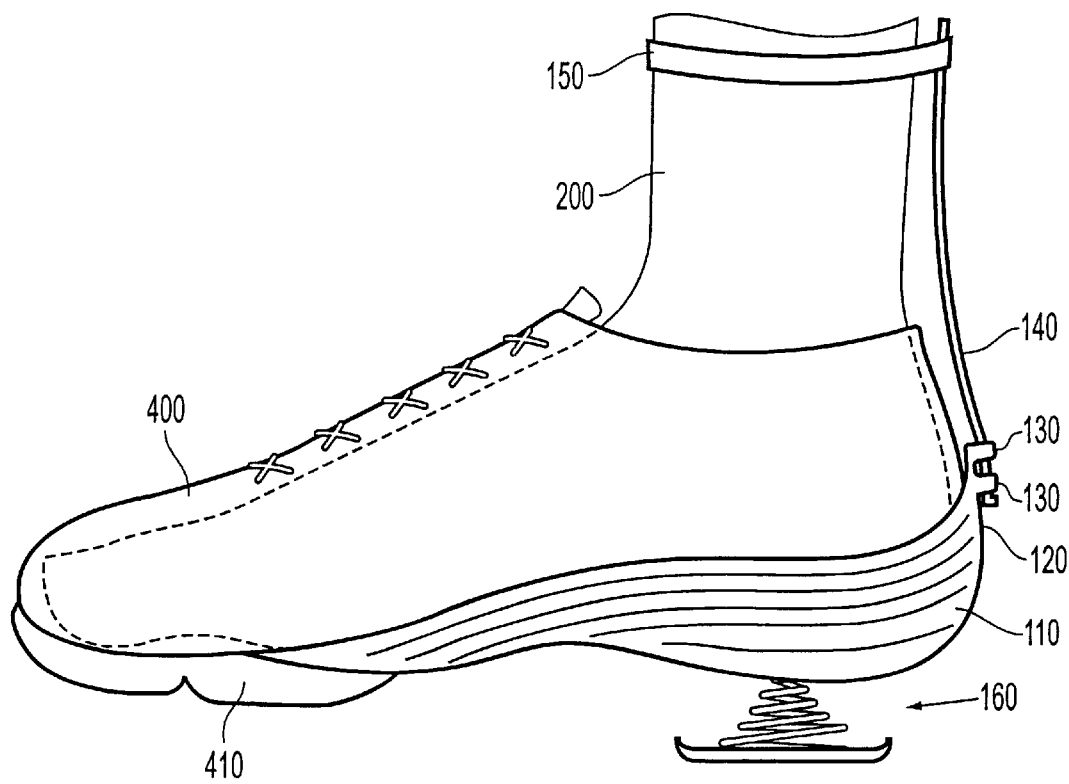
FIG. 4 is a side view of a shoe incorporating the ankle brace according to the invention.

While orthotic plate 110 may be directly fitted to a user's foot and leg by conventional mounting devices (not shown) or worn inside of a wearer's shoe, FIG. 4 shows the illustrative ankle brace 100 integrally fitted into a shoe 400. In this example, orthotic plate 110 serves as a rear sole of the shoe and is fitted onto a shoe upper by conventional techniques, such as molding, sewing, or adhesive. Shoe 400 may include a sole portion 410 that covers the entire lower surface of shoe 400 or may only be provided in a toe portion, with an optional spring heel 160 being provided at a rear of shoe 400. In this embodiment, shoe 400 is a low top shoe with one leg strap serving as support member 150. However, multiple straps may be used, if desired, as illustrated in other views. As shown by the various Figures, the length of blade element 140 is not critical and may be sized to strap around a calf region of leg 200 as shown in FIG. 1 or may be shorter and designed to strap to a lower region of leg 200 as shown in FIG. 4.

While not necessary, straps 150 may be removable from blade element 140. This will allow full removal of blade element 140 from slide support brackets 130 during non-use of the brace. As such, shoe 400 is capable of functioning as a regular shoe as well as an ankle brace. Moreover, by this feature, different blade elements 140 having different characteristic properties may be substituted to change the control of ankle movement of the wearer.

Figure 5:
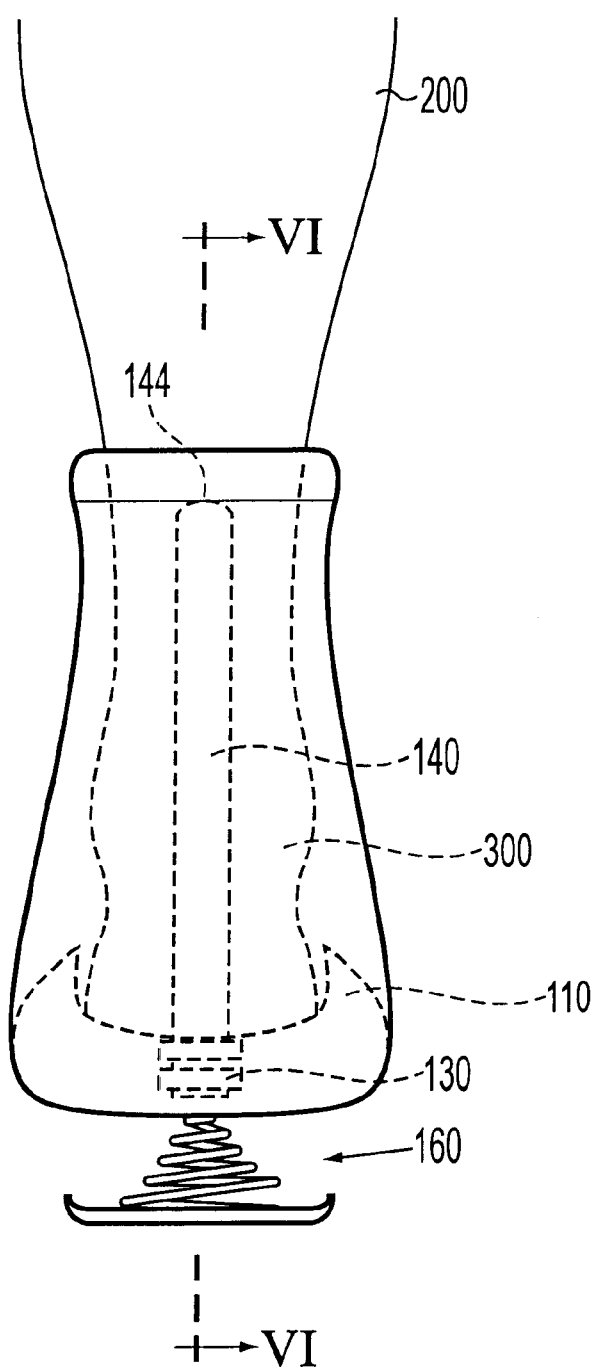
FIG. 5 is a rear view of a shoe with an integrated ankle brace according to the invention.
Figure 6:
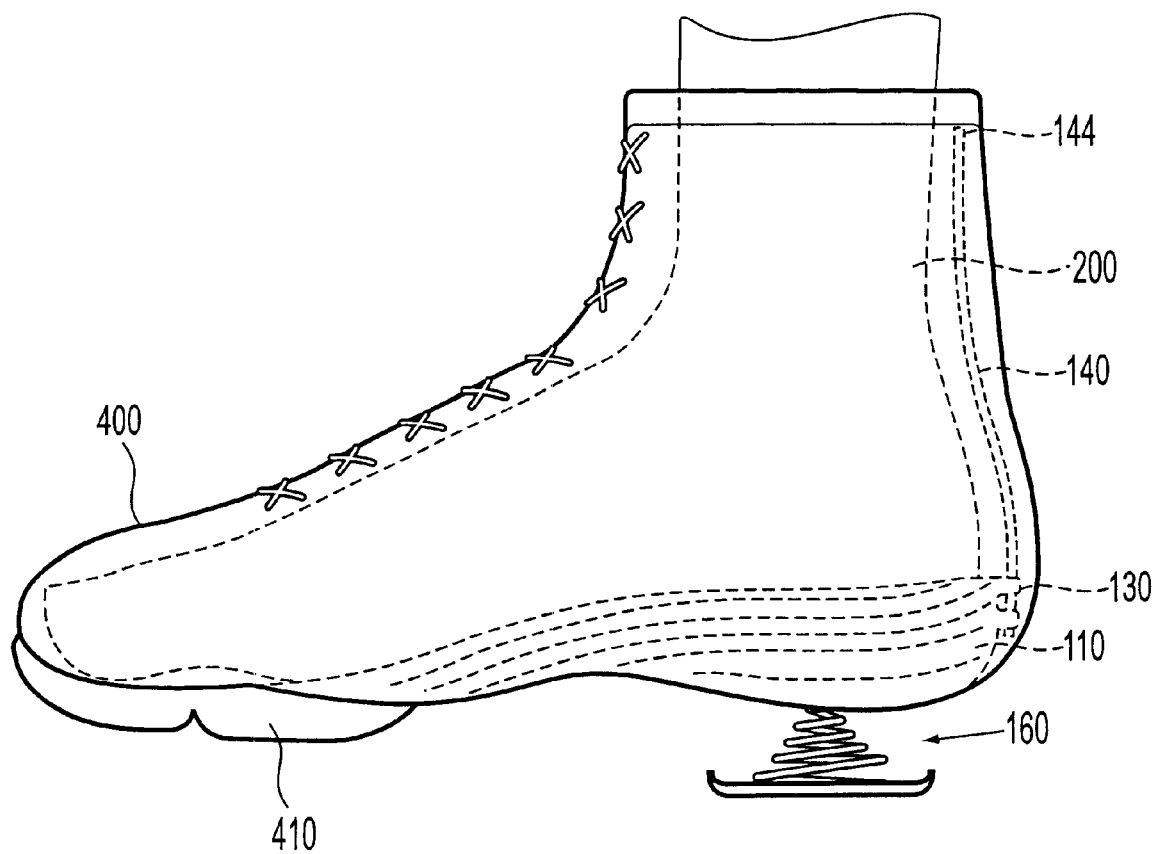
FIG. 6 is a side view of the shoe of FIG. 5 according to the invention.

Another embodiment is shown in FIGS. 5–6 where the shoe 400 is a high top shoe or boot and the ankle brace is incorporated internally in the shoe. That is, slip support bracket 130, blade 140 and support member 150 are located interior of the shoe upper and are not exposed. As shown, bracket 130 may be lower than in the first embodiment. Also, support member 150 may comprise stitching of the distal end 144 into the shoe or the like. This may be accommodated by a widening of distal end 144. For comfort, the ankle brace would include an inner liner (unshown) between the wearer's foot and the ankle brace. As in previous embodiments, the ankle brace severely restricts side-to-side motion of a wearer's ankle while allowing substantially unrestricted forward and rearward leg and ankle motion. This embodiment has the advantage of an ankle brace structure that is unexposed and thus not apparent from the visual appearance of the shoe.

The inventive ankle brace 100 provides an effective mechanism to limit ankle inversion or eversion (side-to-side movement) while allowing a less restricted or unrestricted ability for the ankle to achieve dorsiflexion and plantarflexion movement (up and down). As such, the brace may be used for rehabilitation purposes as well as more strenuous athletic or work purposes where the brace can be used to prevent ankle injuries, such as sprains.

While this invention has been described in conjunction with the specific embodiments outline above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention as defined in the following claims.

What is claimed is:

1. An ankle brace, comprising:
   a semi-rigid orthotic plate shaped to receive a wearer's ankle thereon, the orthotic plate having a rear support portion;
   at least one axial slip support bracket having an opening therethrough fixedly provided on the rear support portion; and
   a longitudinally extending blade element slidably attachable to the at least one axial slip support bracket at a proximal end thereof and fixed relative to a leg of the wearer by at least one support member at a distal end thereof,
   wherein the blade element has an axial length, a thickness T extending in a fore/aft direction of the orthotic plate corresponding to a fore/aft direction of a wearer's foot, and a width W, the ratio of T to W being selected so that the distal end is free to flex about the proximal end in the fore/aft direction and the blade element is substantially constrained from flexure in the width direction, a nominal clearance between the blade element and the opening of the at least one axial slip support bracket being chosen so that slide movement of the blade element through the opening along the longitudinal axis is allowed but lateral movement in the width direction is substantially constrained, the combination of nominal clearance and ratio of T/W controlling restriction of side-to-side ankle movement.

2. The ankle brace of claim 1, wherein the proximal end of the blade element has an increased dimensional size larger than the opening so as to serve as a stop member.

3. The ankle brace of claim 1, wherein the ratio of T to W is selected so as to allow full forward/rearward movement of the wearer's ankle during use of the ankle brace.

4. The ankle brace of claim 3, wherein a free length of blade element extending below the at least one axial slip support bracket allows for between 1–1.5 inches of axial travel of the blade element.

5. The ankle brace of claim 1, wherein the width W and thickness T are substantially uniform along the length of the blade element at least in the vicinity of the proximal end.

6. The ankle brace of claim 1, wherein the rear support portion of the orthotic plate is arcuate with a radius of curvature that generally coincides with a centroid of a wearer's ankle.

7. The ankle brace of claim 6, wherein the radius is about 55 mm.

8. The ankle brace of claim 1, wherein the blade element has a ratio of width W to thickness T of about 11:1.

9. The ankle brace of claim 8, wherein the thickness is about 3 mm.

10. The ankle brace of claim 1, wherein at least one of the blade element and the at least one axial slip support bracket is coated with a low coefficient of friction material.

11. The ankle brace of claim 1, wherein the support member is a leg strap.

12. The ankle brace of claim 1, wherein the clearance is chosen so as to provide substantially no lateral movement of the blade element.

13. The ankle brace of claim 1, wherein the at least one slip support bracket is located slightly below a centroid of the wearer's ankle.

14. The ankle brace of claim 1, wherein a spring serving as a heel portion is affixed to a bottom of the orthotic plate.

15. A shoe having an integrated ankle brace, comprising:
    a semi-rigid orthotic plate shaped to receive a wearer's ankle thereon, the orthotic plate having a rear support portion;
    a shoe upper affixed to the orthotic plate;
    a sole portion located beneath the shoe upper;
    a heel portion located beneath the orthotic plate;
    at least one axial slip support bracket having an opening therethrough fixedly provided on the rear support portion; and
    a longitudinally extending blade element slidably attachable to the at least one axial slip support bracket at a proximal end thereof and fixed relative to a leg of the wearer by at least one support member at a distal end thereof,
    wherein the blade element has an axial length, a thickness T extending in a fore/aft direction of the orthotic plate corresponding to a fore/aft direction of a wearer's foot, and a width W, the ratio of T to W being selected so that the distal end is free to flex about the proximal end in the fore/aft direction and the blade element is substantially constrained from flexure in the width direction, a nominal clearance between the blade element and the opening of the at least one axial slip support bracket being chosen so that slide movement of the blade element through the opening along the longitudinal axis is allowed but lateral movement in the width direction is substantially constrained, the combination of nominal clearance and ratio of T/W controlling restriction of side-to-side ankle movement.

16. The shoe of claim 15, wherein the heel portion includes a spring.

17. The shoe of claim 15, wherein the blade element is removably attached to the at least one axial slip support bracket.

18. The shoe of claim 15, wherein the proximal end of the blade element has an increased dimensional size larger than the opening so as to serve as a stop member.

19. The shoe of claim 15, wherein the ratio of T to W is selected so as to allow full forward/rearward movement of the wearer's ankle during use of the ankle brace.

20. The shoe of claim 15, wherein the rear support portion of the orthotic plate is arcuate with a radius of curvature that generally coincides with a centroid of a wearer's ankle.

21. The shoe of claim 15, wherein the shoe upper covers the blade element.

22. The shoe of claim 15, wherein the distal end of the blade element is fixed to the shoe upper and the shoe upper forms the support member.

23. The shoe of claim 15, wherein a free length of blade element extending below the at least one axial slip support bracket allows for between 1–1.5 inches of axial travel of the blade element.

* * * * *